United States Patent [19]

Kim et al.

[11] Patent Number: 5,559,037

[45] Date of Patent: Sep. 24, 1996

[54] METHOD FOR RAPID AND SIMULTANEOUS ANALYSIS OF NUCLEATED RED BLOOD CELLS

[75] Inventors: Young R. Kim; Michael W. Yee, both of Sunnyvale; Suresh N. Mehta, Pleasanton; Josefino C. Sagala, San Jose; Johanna Kantor, Palo Alto, all of Calif.

[73] Assignee: Abbott Laboratories, Abbott Park, Ill.

[21] Appl. No.: 356,932

[22] Filed: Dec. 15, 1994

[51] Int. Cl.⁶ .................................................. G01N 33/48
[52] U.S. Cl. .................... 436/63; 436/10; 436/17; 436/164; 436/172; 436/175; 435/2; 435/4; 435/29; 435/34; 435/39; 356/39; 356/317; 356/336; 356/337; 356/340
[58] Field of Search ............................. 436/8, 10, 17, 43, 436/52, 53, 63, 164, 172, 174, 175, 800; 435/2, 4, 6, 29, 34, 39; 422/82.05, 82.08, 81, 82; 356/39, 73, 317, 318, 336, 337, 338, 340, 343; 324/71.4

[56] References Cited

U.S. PATENT DOCUMENTS

| | | | |
|---|---|---|---|
| 4,492,752 | 1/1985 | Hoffman et al. | 435/7.21 |
| 4,544,546 | 10/1985 | Wang et al. | 435/6 |
| 4,727,020 | 2/1988 | Recktenwald | 435/6 |
| 4,751,179 | 6/1988 | Ledis et al. | 435/34 |
| 4,882,284 | 11/1989 | Kirchanski et al. | 436/63 |
| 4,978,624 | 12/1990 | Cremins et al. | 436/17 |
| 4,986,657 | 1/1991 | Ohe | 356/73 |
| 4,987,086 | 1/1991 | Brosnan et al. | 436/501 |
| 5,047,321 | 9/1991 | Loken et al. | 435/6 |
| 5,125,737 | 6/1992 | Rodriguez et al. | 356/338 X |
| 5,188,935 | 2/1993 | Leif et al. | 436/63 X |
| 5,298,426 | 3/1994 | Inami et al. | 436/63 |

FOREIGN PATENT DOCUMENTS

| | | |
|---|---|---|
| 0022670 | 1/1981 | European Pat. Off. . |
| 0105614 | 4/1984 | European Pat. Off. . |
| 0121261 | 10/1984 | European Pat. Off. . |
| 94/18828 | 9/1994 | WIPO . |

OTHER PUBLICATIONS

L. W. M. M. Terstappen, et al. "Discriminating Between Damaged and Intact Cells in Fixed Flow Cytometric Samples" Cytometry 9 (1988) Sep., No. 5, pp., 477–484.
Bakker–Schut et al. *Computers & Biomedical Research,* vol. 27, issue 2, 1994, pp. 83–96.
Stewart et al. *Cytometry,* vol. 10, pp. 426–432, 1989.
Leary et al. *Journal of Histochemistry & Cytochemistry,* vol. 24, No. 12, 1976, pp. 1249–1257.

*Primary Examiner*—Jill Warden
*Assistant Examiner*—Maureen M. Wallenhorst
*Attorney, Agent, or Firm*—Richard D. Schmidt

[57] ABSTRACT

A method and a device for the simultaneous and quantitative, flow cytometric analysis of nucleated red blood cells (NRBC) and white blood cells (WBC) in a whole blood sample. The method includes the lysis of red blood cells (RBC) and NRBC cytoplasm from an aliquot of a whole blood sample to eliminate RBC and to expose the NRBC to a vital nuclear stain and the inhibition of the permeation of the nuclear stain into the WBC, subjecting the stained aliquot to flow cytometric light measurements, obtaining at least one signal for parameters including scattered light at a first and a second range of scatter angles and fluorescence (FL), qualifying the obtained signals by using the combination logic wherein a qualified signal must be greater than the second scatter signal threshold, while at the same time it must be greater than either the first scatter signal threshold or the FL threshold {[(first scatter angle signal OR FL signals) AND second scatter angle signal]}, constructing a three-dimensional plot of qualified intensity signals of fluorescence and scattered light from the detected signals, and differentiating the NRBC and WBC from the constructed three-dimensional plot and determining the number of cells of each.

8 Claims, 10 Drawing Sheets

METHOD FOR RAPID AND SIMULTANEOUS ANALYSIS OF NUCLEATED RED BLOOD CELLS

BACKGROUND OF THE INVENTION

This invention relates to a method of differentiating and accurately counting nucleated red cells ("NRBC") in a whole blood sample. In particular this invention relates to a method for the simultaneous differentiation and counting of NRBC and white blood cell ("WBC") sub-populations in a whole blood sample by the use of two light scattering parameters and fluorescence.

Events related to the onset of the anemia need to be carefully monitored. The hematology laboratory offers a set of routine or standard procedures relevant to the diagnosis of anemia. The most important of these procedures are the complete blood count (performed on an automated blood cell counter), blood smear morphology, and the reticulocyte production index. NRBC counts are conventionally determined by means of blood smear morphology. A stained blood smear is examined under the microscope and the NRBC are manually counted. In general, an NRBC concentration is reported as number of NRBC per 100 white blood cells ("WBC"). Normally, 200 WBC and the number of NRBC present in the same region on a patient blood smear are counted and the numbers are divided by 2 to express the NRBC concentration as the number of NRBC/100 WBC. The major drawback to this type of manual microscopic method is that it is very labor intensive, time-consuming, subjective and inaccurate due to poor statistics. Therefore, an accurate automated NRBC method has long been sought after by pathologists and laboratory technicians.

A major problem in automating a NRBC method for use on a clinical flow cytometer has been that since NRBC are rare events and RBC populations are so numerous, NRBC populations are not easily detected among the red blood cell ("RBC") population by either the differences in the cell's electrical resistivity (impedance measurements) or its light scattering characteristics (optical measurements). Although many attempts have been made to count NRBC among WBC populations, instead of among RBC population, these efforts have not generally been successful.

NRBC populations are not easily distinguished from WBC populations since NRBC do not form a well defined cluster among the WBC in the usual two dimensional space differentiation methods utilized on flow cytometers. One is usually not able to separate NRBC populations from the lymphocyte populations when the detected signals are viewed on the generally accepted, two-dimensional light scatter (forward vs. side) or light scatter vs. absorption, dot plots. The signals from the majority of the NRBC population is usually mixed in with the signals for RBC stroma and platelets ("PLT"), and the upper-end of NRBC cluster most often will extend into the space occupied by the lymphocyte population.

Automated clinical hematology instruments, such as the Technicon H*1®, Coulter STK® S and Abbott Cell-Dyn® 3000 and 3500 only "flag" samples for the possible presence of NRBC if the sample dot plot shows increased noise signals below the lymphocyte cluster. This type of flagging very often produces false positive results since the elevated noise level could be due to PLT clumps, giant PLT or incompletely lysed RBC. In addition, it is extremely difficult to obtain accurate Total WBC and WBC Differential ("WBC/Diff") results on samples containing NRBC because of the interference. Additionally, blood smears of the flagged samples must be examined and counted under the microscope by a skilled technician to obtain accurate WBC differential and NRBC counts. This is a very labor-intensive and subjective process.

Recently, U.S. Patent No. 5,298,426, issued on Mar. 29, 1994, to Inami et al. This patent teaches a two-step method comprising the staining of WBC and NRBC by specific nuclear stains. In this patented method, a blood sample is first mixed with an acid hypotonic solution containing a fluorescent nuclear dye. Then, a solution comprising an alkaline salt buffer, to adjust pH and Osmolarity, is mixed with the sample/first reagent solution. This final solution is then loaded into a flow cytometer to detect and count NRBC along with other nucleated cells.

There are several reasons why the Inami et al. approach is not acceptable, especially for an automatable method. First, an acidic-hypotonic solution damages all cell membranes making all WBC leaky and therefore selective staining of NRBC nuclei by a nuclear stain is not possible. There are no known dyes which stain only NRBC nuclei and not WBC nuclei since the nuclear material (DNA) is the same. The nuclear stain claimed by Inami et al., Propidium Iodide, is a commonly used vital nuclear stain that stains dead cell nuclei by permeating damaged cell membrane and intercalates into the DNA helix of any nucleus, not just an NRBC nucleus. Second, the method does not separate or distinguish the fluorescent signals of the NRBC nuclei from that of other nuclear remnants such as Howell-Jolly Bodies, Basophilic Stippling, RNA from lysed reticulocytes and reticulated platelets, and DNA from WBC and Megakaryocytic fragments. Third, the Inami et al. method requires that the sample be pretreated, off-line, using several reagents to "prep" the sample before the prepped sample/reagent solution can be loaded into the instrument.

SUMMARY OF THE INVENTION

A method for the simultaneous and quantitative, flow cytometric analysis of nucleated red blood cells and white blood cells in a whole blood sample is provided. The method comprises the destruction of RBC and NRBC cytoplasm from an aliquot of a whole blood sample to expose the NRBC nuclei to a vital nuclear stain and minimizing the permeation of the vital nuclear stain into the WBC, subjecting the stained aliquot to flow cytometric light measurements, obtaining at least one signal for parameters including scattered light at a first and a second range of scatter angles and fluorescence (FL), qualifying the obtained signals by using the combination logic wherein a qualified signal must be greater than the second scatter signal threshold, while at the same time it must be greater than either the first scatter signal threshold or the FL threshold {[(first scatter angle signal OR FL signals) AND second scatter angle signal]}, constructing a three-dimensional plot of qualified intensity signals of fluorescence and scattered light from the detected signals, and differentiating the NRBC and WBC from the constructed three-dimensional plot and determining the number of cells of each.

In another embodiment of the invention, a device is provided for the simultaneous and quantitative analysis of NRBC and WBC in a whole blood sample. The device comprises a flow cytometer for obtaining at least one signal for parameters including scattered light at a first and a second range of scatter angles and fluorescence (FL or Fl), and a triple triggering circuit that qualifies signals obtained by the flow cytometer for digitation by means of AND/OR logic wherein a qualified signal must be greater than the second scatter signal threshold, while at the same time it must be greater than either the first scatter signal threshold or the FL threshold {[(first scatter angle signal OR FL signals) AND second scatter angle signal]}.

In another embodiment of the invention, a method for the simultaneous and quantitative analysis of nucleated red blood cells and white blood cells in a whole blood sample is provided. The method comprises the elimination of the red blood cells ("RBC") and the cytoplasm of NRBC from an aliquot of a blood sample to expose the NRBC nuclei, staining of the NRBC nuclei with a nuclear stain while minimizing the staining of WBC, subjecting the aliquot to flow cytometric light measurements, obtaining at least one signal for parameters including scattered light extinction at from about 0° to about 1° (ALL), scattered light from about 3°–10° (IAS) and fluorescence (Fl), qualifying the signals obtained by using AND/OR logic wherein the logic comprises [(ALL signals) OR (Fl signals) AND (3°–10° scatter signals)], constructing a three-dimensional plot of qualified intensity signals of fluorescence and scattered light from the detected signals, and differentiating the NRBC and WBC from the constructed three-dimensional plot and determining the number of cells of each.

In another embodiment of the invention, a flow cytometric device is provided for the quantitative analysis of nucleated red blood cells and white blood cells in a whole blood sample. The device comprises a flow cytometer for obtaining at least one signal for parameters including scattered light at from about 0° to about 1° and from about 3°–10° and fluorescence (Fl) and a triple triggering circuit that qualifies signals obtained by the flow cytometer for digitation by means of AND/OR logic wherein the logic comprises [(0° to about 1° scatter signals) OR (Fl signals) AND (3°–10° scatter signals)] to validate signals for further processing.

DETAILED DESCRIPTION OF THE INVENTION

Figure 1:
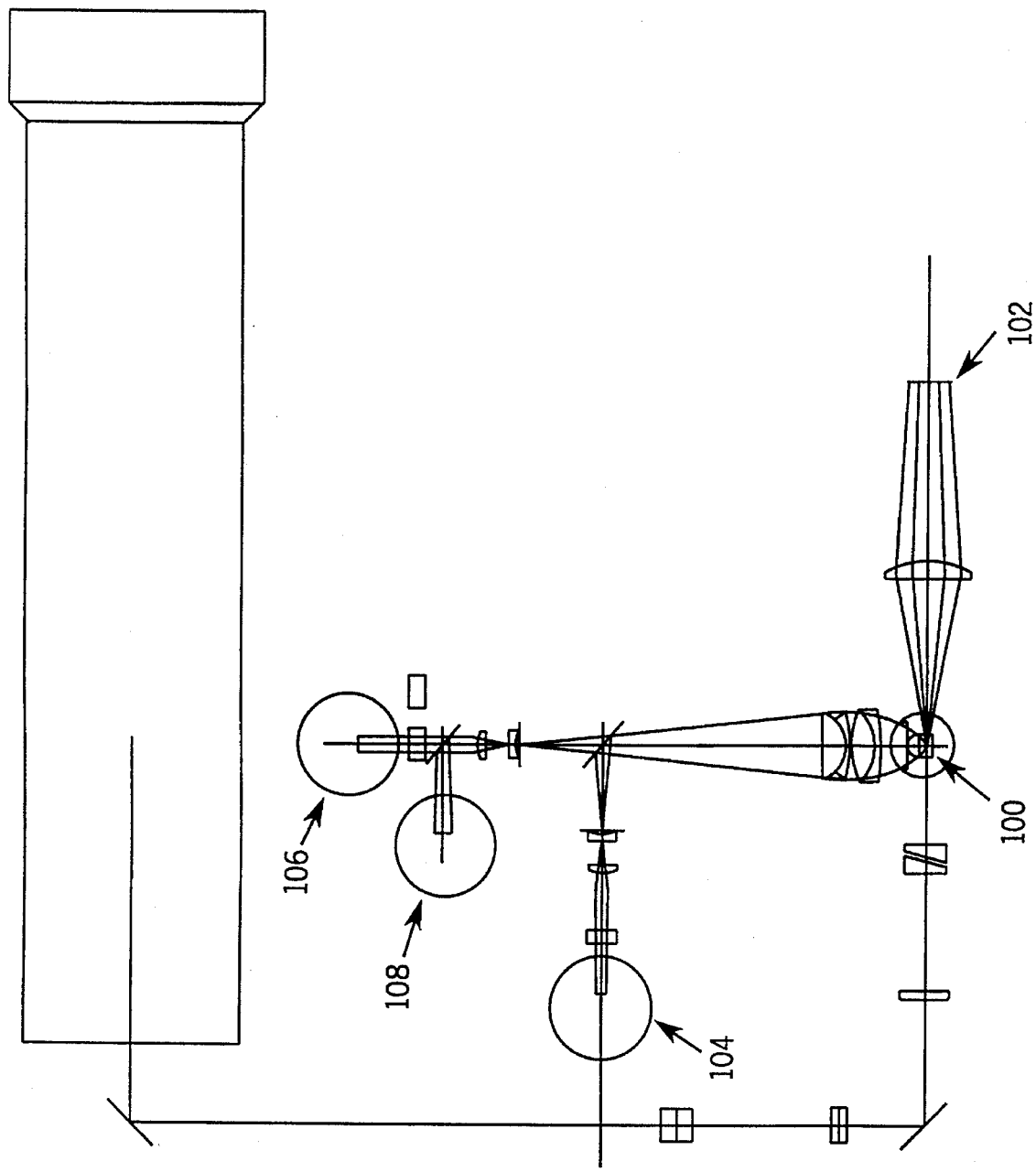
FIG. 1 is a schematic diagram of the optics of a clinical flow cytometer that may be employed in implementing the method of the present invention.

Broadly, the present invention relates to an automated method for simultaneous analysis of WBC/Diff and NRBC in a whole blood sample using a unique triple triggering method. This method enables accurate NRBC counts and WBC/Diff data, simultaneously from a whole blood sample containing NRBC.

An important aspect of the present invention is that the signals from debris (both fluorescent and non-fluorescent) are blocked by the triple triggering method and the signals which fall below the ALL trigger but above the FL3 trigger can be identified and counted as NRBC. Therefore, accurate NRBC counts, which are essentially free of contamination from fluorescent nuclear debris, are obtained. Fragile blast cells and dead cells may also be detected utilizing the methods of this invention.

In the triple trigger method, it is possible to simultaneously count WBC/Diff and NRBC accurately by mixing the blood sample with a blood diluent which rapidly lyses RBC and preserves WBC, and to which has been added a suitable nuclear stain which will stain naked nuclei of the NRBC. Such a diluent is disclosed in U.S. application Ser. No. 08/297,662, entitled "MULTIPURPOSE REAGENT SYSTEM FOR RAPID LYSIS OF WHOLE BLOOD SAMPLES", filed on Aug. 29, 1994 and now U.S. Pat. No. 5,516,695 issued May 14, 1996, and herein incorporated by reference thereto. The diluent/sample mixture is then passed, essentially a cell at a time through an illuminated optical flow cell. This causes the cells to scatter the illuminating light and any stained nuclei present to fluoresce. The scattered and fluorescent light signals are detected by known means and, by using the triple triggering method in conjunction with the processing of the detected signals it is possible to identify and quantify WBC, WBC/Diff and NRBC. A hematology analyzer which has been found to be particularly compatible with the triple trigger method of this invention is disclosed and described in U.S. application Ser. No. 08/283,379, entitled "METHOD AND APPARATUS FOR PERFORMING AUTOMATED ANALYSIS", filed on Aug. 1, 1994 and now abandoned, and is herein incorporated by reference thereto.

The triple trigger method is unique in that the simultaneous analysis of WBC/Diff/NRBC can be carried out automatically, accurately, and rapidly without interference from other cellular debris such as RNA from lysed reticulocytes, Howell Jolly Bodies, reticulated platelets, giant platelets, DNA from WBC and Megakaryocytic fragments, parasites, and RBC fragments. Further advantage of the present invention is that it has a very high clinical value in that the method can be incorporated into a clinical hematology analyzer which routinely calibrate for WBC, RBC, and Platelet counts. Such a system is capable of producing an accurate WBC/Diff/NRBC data (percent as well as absolute counts) in clinical blood samples. This has not previously been possible.

The triple trigger method also permits accurate WBC/Diff analysis in a blood sample that contains NRBC by subtracting signals identified as NRBC from the total WBC signals before WBC/Diff analysis is performed. Only one dye is needed for NRBC staining and the WBC/Diff analysis can be performed by the difference of light scattering characteristics of the WBC subclasses.

The present invention achieves all of the objectives described above by a unique triple triggering method in the three dimensional space of Axial Light Loss (ALL), Intermediate Angle Scatter (IAS) and Red Fluorescence (FL3).

To accomplish this, one or more detectors are preferably placed in the forward light path for measuring forward intermediate angle scattering (IAS) and either small angle forward scattering (SAS) or axial light loss (ALL, also known as forward extinction). ALL is generally the decrease in light energy due to a cell passing in front of a laser beam and being detected by a photodiode. The light loss is generally due to scattering and defined as the decrease in light energy reaching a detector in the path of a laser beam due to the passage of a cell through that beam (generally ALL is detected at an angle of from about 0° to about 1°.) Small angle forward scatter (SAS), in contrast, is light energy that reaches a detector outside (but within a narrow angle of about 1° to 3°) the incident laser beam due to scattering from a cell passing through the beam. A beam stop is generally provided to keep the laser beam from getting into the detector. ALL measuring systems collect light within the incident cone of laser illumination, while small angle scatter systems collect light outside this cone. In ALL measuring systems, the signal of interest is a negative signal subtracted from the steady state laser signal, whereas in small angle forward scatter measurement the signal is a small positive signal imposed on a very low background light level. Intermediate angle forward scattering (IAS) is similar to small angle forward scattering, except the light is scattered at a larger angle from the incident laser beam. More specifically, IAS relates to light scattered in a ring between about 3° and 10° away from the incident or center line of a laser beam. In a preferred embodiment, ALL is collected in the angles less than about 0.3° horizontally and less than about 1.2° vertically from the laser axis, and IAS is collected at angles between about 3° and 10° from the laser axis.

Another technical advantage of the disclosed system is that it requires much lower concentration of the dye to effectively and rapidly stain NRBC for accurate detection and counting because of complete lysis of the cytoplasm of NRBC making their nuclei more accessible to the stain. This condition permits high signal to noise (S/N) ratio, greater than 100, in NRBC detection. The concentration of a vital dye required in this system to rapidly perform the simultaneous analysis of WBC/Diff/NRBC is only 1 to 2 µg/ml which is at least 50 fold less than that in the previous art.

Vital stains (nuclear stains which stain only dead or damaged cells) that can be used in the present invention can be any vital stain with relatively high extinction coefficient and low fluorescence intensity when they are not bound to nucleic acid. The spectral characteristics, i.e. Extinction (EX) max. (nm)/Emission (EM) max. (nm), of the vital dyes must be compatible with the laser light source used in the system.

The following characteristics are desired for the vital stains for the disclosed system:

High extinction coefficient

High quantum yield

High binding affinity to nucleic acid

Low fluorescence when it is not bound to nucleic acid

Light source compatibility of Spectral Characteristics. (e.g. EX max.~488 nm and EM max.~630 nm with an Argon laser light source.)

There are a number of nuclear dyes qualified for use in the disclosed system with appropriate light source. Some of the commercially available dyes that can be used in the disclosed system are YOYO-1, YOYO-3, TOTO-1, TOTO-3, BO-PRO-1, YO-PRO-1, TO-PRO-1, and many more. It is known to those who are familiar in the art that the dyes with different EX max. can be excited with appropriate light source such as He-Ne, Xenon or Mercury lamps.

Qualified dyes which can be used with an Argon laser which are also commercially available are Propidium iodide (PI), ethidium bromide (EBr), ethidium homodimer-1 (EthD-1), ethidium homodimer-2 (EthD-2) or diethylene triamine (DTA). In one application of the present invention, the vital stain used is PI. A multipurpose reagent system (U.S. application Ser. No. 08/297,662) having a pH of about 6.5, osmolarity of about 260, and comprises an acetate buffer (about 15 mM), ammonium chloride (about 5.0 g/L), potassium bicarbonate (about 2 g/L), saponin (about 100 mgs/L) and formaldehyde (about 0.07%) is used to carry-out a one-step simultaneous analysis of WBC/Diff/NRBC at about 42° C. within one minute.

U.S. patent application Ser. No. 08/283,379, entitled "METHOD AND APPARATUS FOR PERFORMING AUTOMATED ANALYSIS", filed on Aug. 1, 1994 and now abandoned, and incorporated herein by reference, discloses an automated Hematology analyzer which utilizes light scatter signals ALL and IAS, among others, as well as various fluorescent signals to differentiate cells and subclasses of cells from a whole blood sample. The following description is defined by this hematology analyzer. Such a description is merely for convenience and by no means is the present invention limited to only one instrument.

A portion of a whole blood sample, about 25 microliters, is deposited by means of a sample aspiration probe into the WBC cup which contains about 850 microliters of an isotonic lysing reagent. A lysing reagent is used to lyse the erythrocyte fraction of the blood sample and to lyse the cytoplasm of NRBC to expose the nuclei of any NRBC present. In addition to lysing the erythrocyte fraction of the blood, the reagent must be gentle enough to protect or not damage the WBC fraction. One such lysing reagent system is disclosed in U.S. patent application Ser. No. 08/297,662, entitled "MULTIPURPOSE REAGENT SYSTEM FOR RAPID LYSIS OF WHOLE BLOOD SAMPLES", filed on Aug. 29, 1994 and now U.S. Pat. No. 5,516,695 issued May 14, 1996, and is herein incorporated by reference. This reagent system is characterized in that it embodies a one reagent/one step process that achieves multipurpose goals. This reagent is gentle enough to preserve the morphology of all fragile white cells, and at the same time efficiently lyse all of the red cells. Both of these goals are accomplished even in hemaglobinophathic samples, which may require that the lysing time be extended. No matter what the formulation of the lyse utilized with the triple trigger method, the reagent will additionally contain, or be combined with, a small concentration of a vital nuclear stain which effectively labels any NRBC which might be present in the peripheral blood. Preferably, for use with the above referenced analyzer, the lysis chemistry will be configured such that the refractive index matches that of a sheath solution to substantially less than 0.1%.

The mixture of lyse reagent and sample will normally remain in the above referenced WBC cup only for 11 seconds. There it is lysed and mixed at 42° C. ±3° C. At this point, the contents of the WBC cup are piped directly to an optical flowcell 100 for detection, see FIG. 1.

The measurement process begins as the cell stream passes through the flowcell 100, having been diluted with the addition of lyse so that the cells pass through the laser illuminated volume single file, in a laminar flowing sample stream surrounded by diluent/sheath solution. The illuminated volume is bounded in the two dimensions normal to the flow axis by the hydrodynamically focused cell stream, and in the dimension parallel to the flow axis by the vertical beam waist of the laser beam which is about 17 microns. When doing this test, the sample flow rate is about 2.5 microliters per second, and the corresponding illuminated sensing volume of the WBC and NRBC cells approximates an elliptical cylinder with dimension of about 80×5×17 microns. The 17 micron dimension is measured along the axis of the cylinder.

Figure 2:
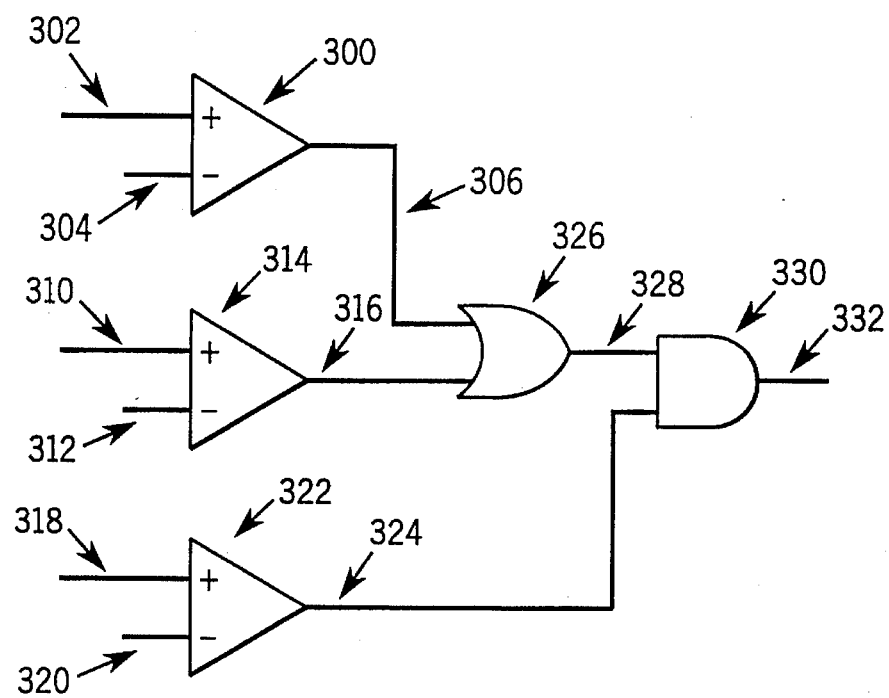
FIG. 2 is a diagram depicting a "Valid" triple trigger circuit.

At this point and as shown in FIG. 1, the presence of a cell is detected by a compound photodiode 102 detecting axial light loss (ALL) and intermediate angle scatter (IAS), photomultiplier tube 104 which detects red fluorescence, and a unique triple trigger circuit, shown in FIG. 2, in the three dimensional feature space of ALL, IAS, and FL3 (red fluorescence). The triple trigger circuit qualifies signals for digitization using AND/OR logic. A qualified signal must be greater than the IAS trigger, while at the same time it must be greater than either the ALL trigger or the FL3 trigger. The combination of this unique triggering circuit, and the lysing properties which include a balanced fixative, allow the exposed NRBC nuclei to be rapidly stained, and clearly and non ambiguously counted and excluded from the WBC differential cell count without the usual interference from background, both fluorescent and non-fluorescent, such as DNA fragments, RBC stroma, and platelets.

One or more detectors are preferably placed in the forward light path for measuring forward intermediate angle scattering (IAS) and either small angle forward scattering (SAS) or axial light loss (ALL, also known as forward extinction). ALL is generally the decrease in light energy due to a cell passing in front of a laser beam and being detected by a photodiode. The light loss is generally due to scattering and defined as the decrease in light energy reaching a detector in the path of a laser beam due to the passage of a cell through that beam (generally ALL is detected at an angle of from about 0° to about 1°.) Small angle forward scatter (SAS), in contrast, is light energy that reaches a detector outside the incident laser beam (but within a narrow angle of from about 1° to 3°) due to scattering from a cell passing through the beam. A beam stop is generally provided to keep the laser beam from getting into the detector. ALL measuring systems collect light within the incident cone of laser illumination, while small angle scatter systems collect light outside this cone. In ALL measuring systems, the signal of interest is a negative signal subtracted from the steady state laser signal, whereas in small angle forward scatter measurement the signal is a small positive signal imposed on a very low background light level. Intermediate angle forward scattering (IAS) is similar to small angle forward scattering, except the light is scattered at a larger angle from the incident laser beam. More specifically, IAS relates to light scattered in a ring between about 3° and 10° away from the incident or center line of a laser beam. In a preferred embodiment, ALL is collected in the angles less than about 0.3° horizontally and less than about 1.2° vertically from the laser axis, and IAS is collected at angles between about 3° and 10° from the laser axis.

When cells, thus triggered, pass through the aforementioned illuminated volume, pulses are generated at detectors 102, 104, 106 and 108. The amplitudes of these pulses are then filtered, amplified, digitized, and stored in list mode in the corresponding five dimensional feature space of ALL, IAS, FL3, PSS (polarized side scatter), and DSS (depolarized side scatter). The normal counting time through flowcell 100 is 10 seconds. At the flow rate and dilution ratio described above, with a normal patient WBC count of 7000 cells per microliter of blood volume, the resulting event count rate would be 5000. In low count samples, this counting time can be automatically extended in order to improve the statistics of the measurement.

At the conclusion of the measurement time, the sample stream is piped to waste, and probe is cleaned and dried and prepared to process a subsequent sample.

Algorithms are then applied to the list mode data of the aforementioned feature space of ALL, IAS, FL3, PSS, and DSS, and the following cell types are enumerated and/or flagged within less than 30 seconds of processing time:

| CELL TYPES ENUMERATED | PERCENTAGES | FLAGGED OR ENUMERATED |
|---|---|---|
| White Cell concentration | (WBC) | |
| Neutrophil concentration | % N of WBC | |
| Lymphocyte concentration | % LYMPH of WBC | |
| Monocute concentration | % MONO of WBC | |
| Eosinophil concentration | % EOS of WBC | |
| Basophil concentration | % BASO of WBC | |
| NRBC | % NRBC of WBC | |
| Band concentration | | (BAND) |
| Blast concentration | | (BLST) |
| Immature gran. conc. | | (IG) |
| Variant-lymph conc. | | (VARL) |

ALL and IAS signals are detected and collected for the WBC/Diff analysis and FL3 signals from stained NRBC nuclei are collected for NRBC analysis, as will be described below. The triple trigger circuit, shown in FIG. 2, qualifies these signals for digitization using AND/OR logic. To be qualified a signal must be greater than the IAS trigger, while at the same time it must be greater than either the ALL trigger or the FL3 trigger.

The various components and generated or utilized signals identified in FIG. 2 correspond to the following labels:
300—ALL Voltage Comparator
302—ALL Signal
304—ALL Threshold Voltage (Vth1)
306—ALL Voltage Comparator Output
310—FL3 Signal
312—FL3 Threshold Voltage (Vth2)
314—FL3 Voltage Comparator
316—FL3 Voltage Comparator Output
318—IAS Signal
320—IAS Threshold Voltage (Vth3)
322—IAS Voltage Comparator
324—IAS Voltage Comparator Output
326—OR Gate
328—OR Gate Output
330—AND Gate
332—Valid Trigger Output Real time signals from their respective channels are present at the inputs of the voltage comparators. Voltage comparators 300, 314 and 322 function by comparing the "+ inputs" (302, 310 and 318) to the "− inputs" (304, 312 and 320) to resultant outputs (306, 316, 324). If the "+ input" is of a higher voltage than the "− input" the output will be high. If the "+ input" is of a lower voltage than the "− input" the output will be low.

The threshold voltages are independent voltages which are determined by system parameters.

The outputs of comparators 300 and 314 are inputs to OR gate 326 to give resultant OR gate output 328. The OR gate functions by comparing its inputs. The output will be high if either, or both, inputs are high.

The output 324 of the OR gate 328 and the output of comparator 322 are inputs to AND gate 330. The AND gate functions by comparing its inputs to derive its output 332 which is also the valid trigger output. The output will be high only if both inputs are high.

The valid trigger output 332 will only be high if the IAS signal 318 is greater than its threshold voltage 320, and either or both, the ALL signal 302 is greater than its threshold voltage 304 or the FL3 signal 310 is greater than its threshold voltage 312.

Figure 14A:
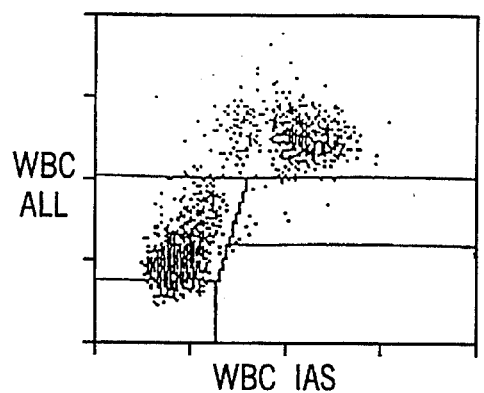
FIGS. 14A, 14B and 14C depict the distribution of a whole blood sample which contained 56 NRBC/100 WBC utilizing the triple trigger (ALL, FL3 and IAS) detection method of the present invention.
Figure 14B:
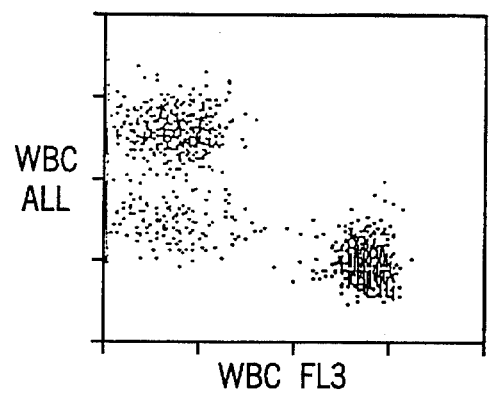
Figure 14C:
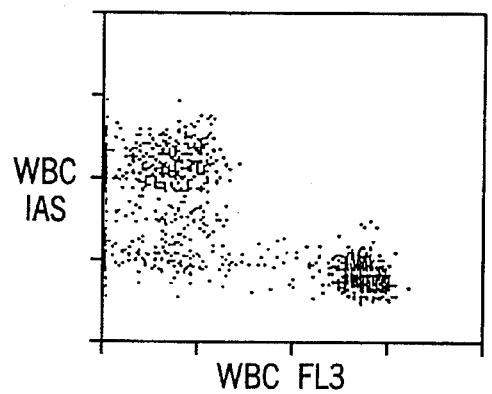
Figure 15A:
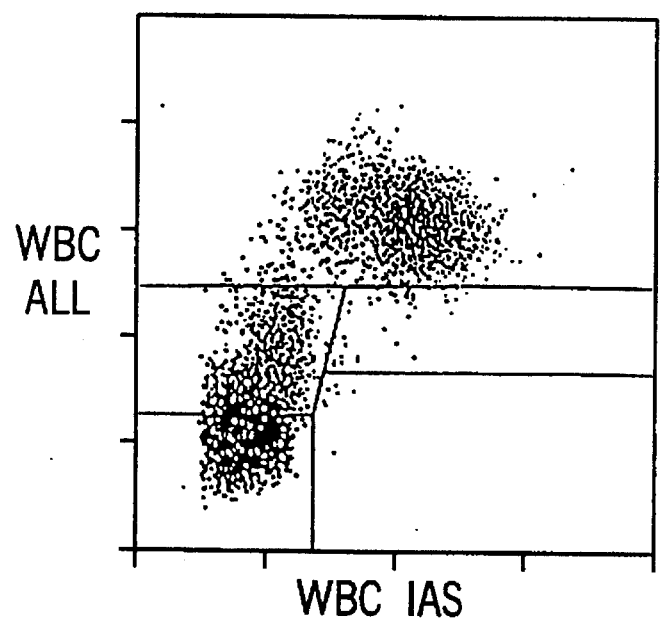
FIGS. 15A and 15B depict the distribution of another whole blood sample which contained 140 NRBC/100 WBC, also utilizing the triple trigger (ALL, FL3 and IAS) detection method of the present invention.

Using the above triggering circuit, the NRBC's form a unique cluster in the aforementioned three dimensional space, see FIGS. 14 and 15, which can be easily counted during the Optical WBC Differential analysis, and exclude non ambiguously from the WBC count. Thus, a count of NRBC per 100 WBC, and an absolute NRBC per μl of patient blood is reported. Consequently, NRBC are subtracted from total WBC counts permitting accurate total WBC and Differential analysis in the presence of NRBC in a blood sample. Background noise, both fluorescent and non-fluorescent, from DNA fragments, RBC stroma, platelets, Howell-Jolly Bodies, Basophilic Stippling, RNA from lysed reticulocytes and DNA from WBC and Megakaryocytic fragments are substantially eliminated. Stained NRBC nuclei are separated from the various background noise signals via the disclosed triple-triggering process (on ALL, IAS and FL3) and only the FL3+ signals from NRBC nuclei above the FL3 trigger on the ALL vs. FL3 dot plot are counted as NRBC.

In FIGS. 3A, 3B and 3C through 10A, 10B and 10C the cell population areas identified by the below listed numbers, correspond to the following cell types:
202=Lymphocytes
204=Monocytes
206=Granulocytes
208=Origin Noise
210=NRBC
212=Stroma

EXAMPLE 1

An EDTA-anti-coagulated fresh normal blood was run on an experimental unit of the automated clinical hematology analyzer described above and disclosed in U.S. patent application Ser. No. 08/283,379, entitled "METHOD AND APPARATUS FOR PERFORMING AUTOMATED ANALYSIS", filed on Aug. 1, 1994 and now abandoned, and incorporated herein by reference. While the present invention was incorporated into the aforementioned analyzer it was not always utilized in all of the following examples. Twenty five (25) micro-liters of the blood sample were mixed on-line with 675 micro-liters of the isotonic multi-purpose reagent (pH 6.5, 260 mOsm/L) disclosed in U.S. application Ser. No. 08/297,662, entitled "MULTIPURPOSE REAGENT SYSTEM FOR RAPID LYSIS OF WHOLE BLOOD SAMPLES", filed on Aug. 29, 1994 and now U.S. Pat. No. 5,516,695 issued May 14, 1996, and herein incorporated by reference.

For the purposes of these experiments the multipurpose reagent system is comprised of about 95 mM ammonium chloride (5 g/l), about 0.075% by volume of formaldehyde, from about 10 mM to about 20 mM acetate buffer, about 10 mM potassium bicarbonate, and about 0.01% by weight volume (i.e., grams per 100 ml) of saponin. The pH of the reagent system is adjusted to a range of from about 6.2 to about 7.0 and the osmolality of the reagent system is from about 215 to about 270 mOsm/L.

The reagent is pre-warmed at 42° C. ±3° in the instrument's heated mixing chamber, where the sample and reagent are mixed and incubated for 11 seconds. This mixture was then transported to the flow cell (which takes 8 and ½ seconds) for the WBC/Diff/NRBC analysis. The optical configuration of the system is presented in FIG. 1. The analysis was performed without implementing the triple triggering circuit; using only ALL and FL3 dual triggers as is common in the art. See FIGS. 3A, 3B, and 3C through 10A, 10B and 10C.

Figure 11A:
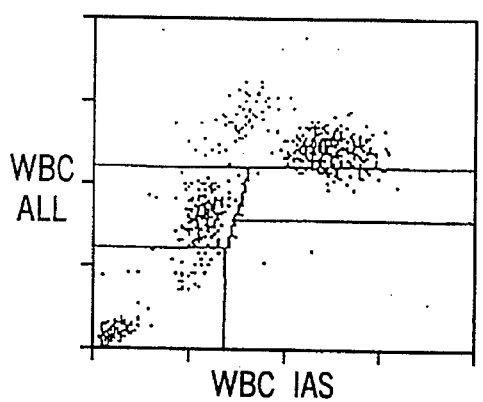
FIGS. 11A, 11B and 11C show the dot plot displays of a normal blood sample processed as described in EXAMPLE 1, utilizing normal or standard detection triggers.
Figure 11B:
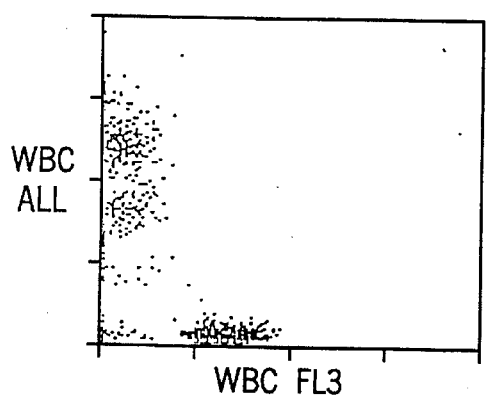
Figure 11C:
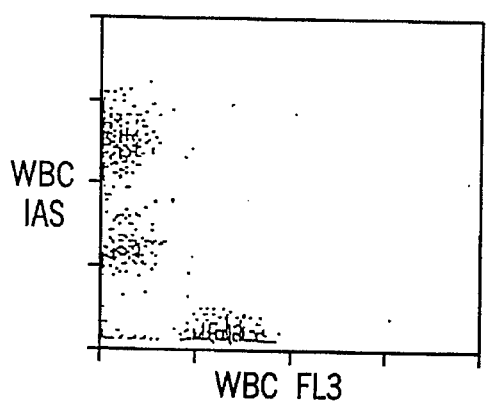

The upper dot plot display in FIGS. 11A, 11B and 11C map the light scatter signals (ALL vs. IAS) obtained from the sample and show 3 distinct populations of WBC. The Basophil cluster is not apparent here because normal bloods do not contain many Basophils. The Eosinophil cluster is not shown here since Eosinophils are separated via a DSS vs. PSS dot plot (not shown) and the middle cytogram is a dot plot display of ALL and FL3 signals as labeled. Note that normal bloods do not contain any NRBCs. The lower bottom FL3+ cluster is apparently cell debris containing RNA or DNA, as described earlier.

EXAMPLE 2

Figure 12A:
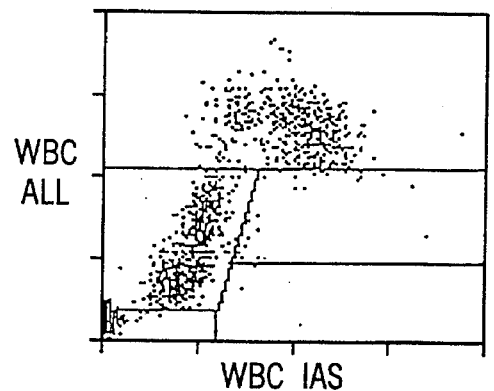
FIGS. 12A and 12B show the cytograms of an abnormal blood with NRBC, processed as described in EXAMPLE 2, utilizing standard or normal detection triggers.
Figure 12B:
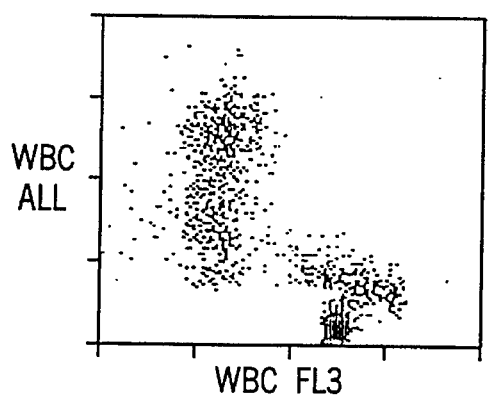

FIGS. 12A and 12B top and bottom cytograms are dot plot displays of an abnormal blood with NRBC (47 NRBC/100 WBC) analyzed as described in EXAMPLE 1 utilizing a standard detection method. The cluster right below the lymphocyte population in the top cytogram belongs to NRBC and the small cluster at the bottom, left corner belongs to the origin noise which include RBC stroma (reticula, Howell Jolly Bodies and etc.), platelets and WBC debris. The bottom cytogram shows that the origin noise cluster of this sample stained with the nuclear dye brightly, following the stained NRBC cluster very closely in FL3 channel, thereby making it impossible to set the FL3 trigger to count NRBC accurately.

EXAMPLE 3

Figure 13A:
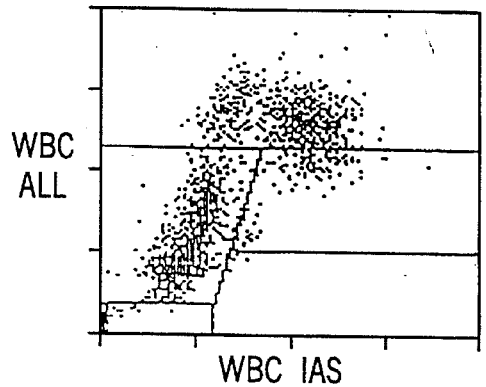
FIGS. 13A and 13B show the cytograms of an abnormal blood with NRBC, processed as described in EXAMPLE 3, utilizing normal detection triggers.
Figure 13B:
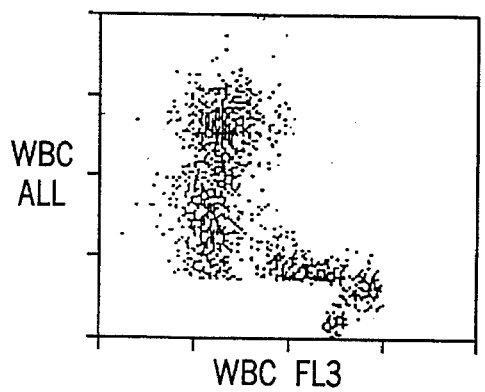

The cytograms for FIGS. 13A and 13B are dot plot displays of an abnormal blood with NRBC (51 NRBC/100 WBC) analyzed as described in EXAMPLE 1 utilizing a standard detection method. The cluster right below the lymphocyte population in the top display belongs to NRBC. An increased FL3+ origin noise of this sample can be seen. The noise cluster is located very close to the NRBC cluster in the FL3 channel. Thus, the FL3 noise is interfering with the position of the FL3 trigger. When the FL3 trigger was set high enough to eliminate all the origin noise, a part of the NRBC population was also lost below the FL3 trigger as shown in the bottom display.

EXAMPLE 4

The disclosed triple trigger circuit (ALL/IAS/FL3) of the present invention was incorporated into the same instrument used in EXAMPLES 1 through 3 and utilized during this procedure. A EDTA, anti-coagulated clinical sample which contained 56 NRBC/100 WBC was processed as described in EXAMPLE 1. The results are presented in FIGS. 14A, 14B and 14C. Note the disappearance of the FL3+ noise cluster. The noise signals are blocked by the added IAS trigger. The fluorescent origin noise from this abnormal blood is no longer visible above the FL3 trigger, although the trigger is set low enough to recover the total NRBC population. (Note the circular shape of the NRBC cluster.)

EXAMPLE 5

Figure 15B:
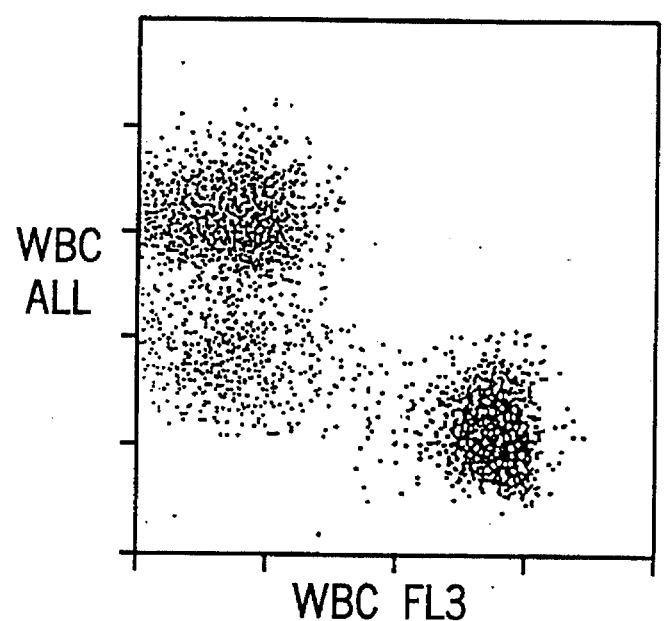

FIGS. 15 and 15B show the dot plot displays of the NRBC distribution of another clinical whole blood sample which contained 140 NRBC/100 WBC, also post triple trigger (ALL, FL3 and IAS) implementation. The origin noise is not visible and the total NRBC population is recovered above the FL3 trigger. Note the heavy density of the NRBC cluster due to the very high concentration of NRBC in this sample.

EXAMPLE 6

Figure 16A:
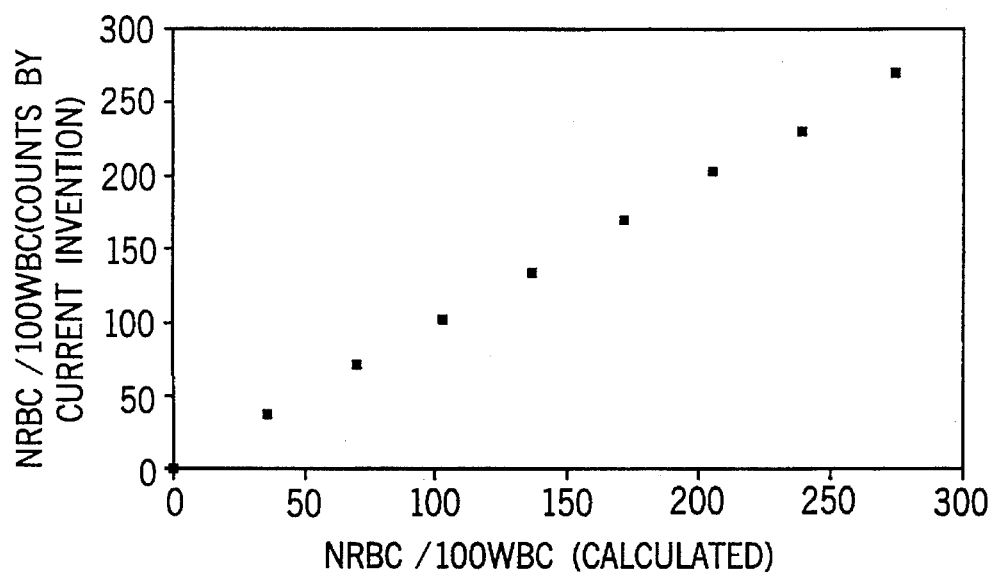
FIGS. 16A and 16B show the results of linearity samples that were prepared and processed as described in EXAMPLE 6 by utilizing a method of the present invention.
Figure 16B:
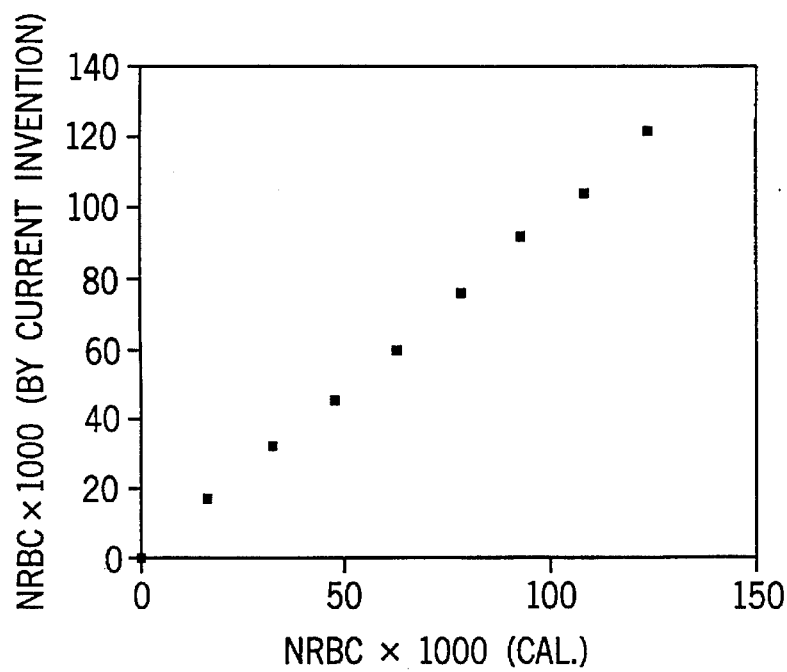

Linearity samples were prepared by adding various concentrations of unfixed chicken erythrocytes to a EDTA, anti-coagulated normal human blood. The samples were processed as described in EXAMPLE 1 utilizing the triple trigger detection method of the present invention. The cytoplasm of chicken erythrocytes lyse in the method of present invention leaving only naked nuclei (CEN). The CEN stained very rapidly with the vital nuclear stain (PI) in the diluent and become fluorescent (FL3). The FL3+ CEN are counted as NRBC and reported as number of NRBC/100 WBC and as absolute counts per µL of the whole blood sample in the method of the present invention. The results are presented in FIGS. 16A and 16B. The linearity plots of NRBC/100 WBC and NRBC in absolute numbers in the figure demonstrate that the method of the current invention generate a linear NRBC counts.

EXAMPLE 7

Figure 17:
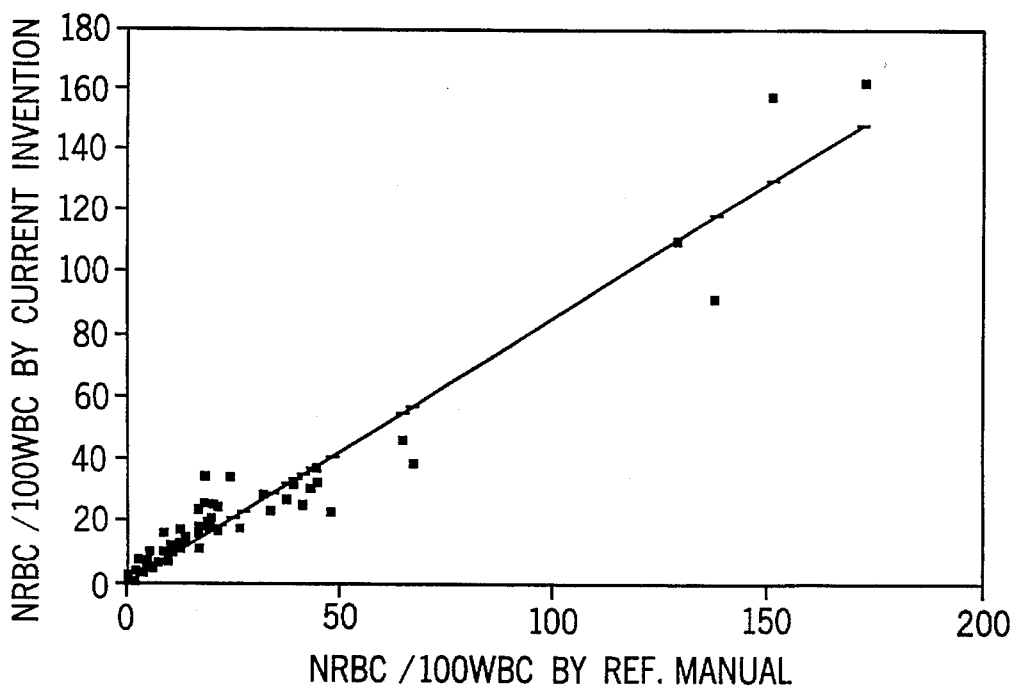
FIG. 17 is the correlation plot of an automated hematology analyzer's NRBC counts (ordinate) utilizing a method of the present invention and manual microscopic NRBC counts (abscissa). The data were processed as described in EXAMPLE 7.
Figure 3A:
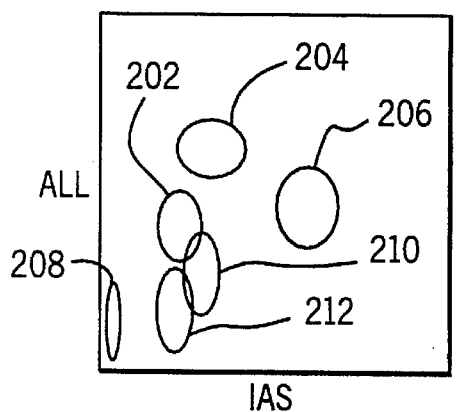
FIGS. 3A, 3B and 3C are drawings of the WBC, NRBC, RBC stroma and other background noise distribution of a whole blood sample processed as described in EXAMPLE 1, utilizing standard or normal detection triggers.
Figure 4A:
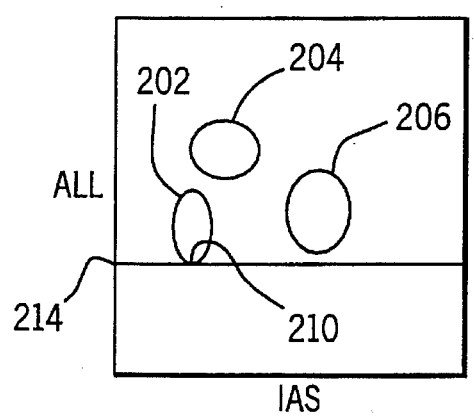
FIGS. 4A, 4B and 4C are drawings of the WBC, NRBC, RBC stroma and other background noise distribution of a whole blood sample processed as described in EXAMPLE 1 utilizing only an 0° to about 1° scatter axial light loss (ALL) trigger.
Figure 3B:
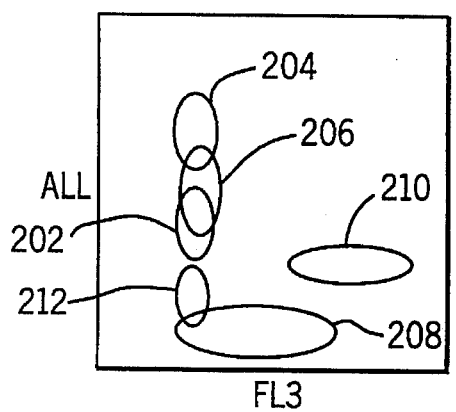
Figure 4B:
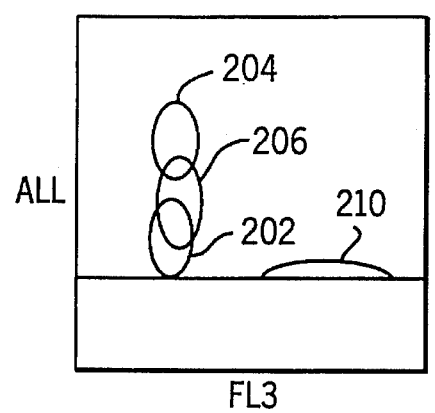
Figure 3C:
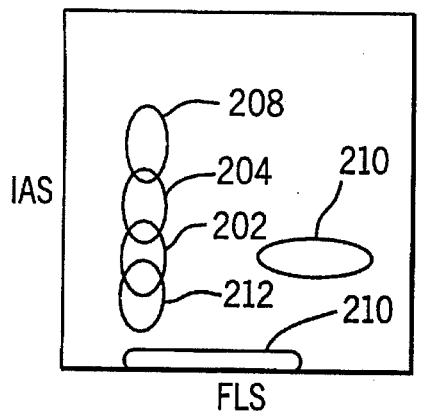
Figure 4C:
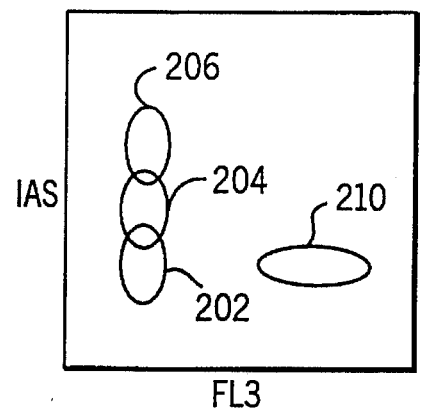
Figure 5A:
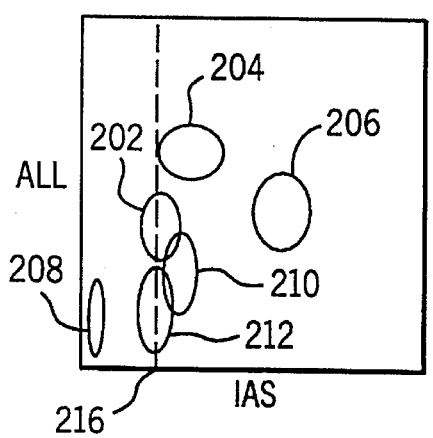
FIGS. 5A, 5B and 5C are drawings of the WBC, NRBC, RBC stroma and other background noise distribution of a whole blood sample processed as described in EXAMPLE 1 utilizing only a 3°–10° intermediate angle scatter (IAS) trigger.
Figure 6A:
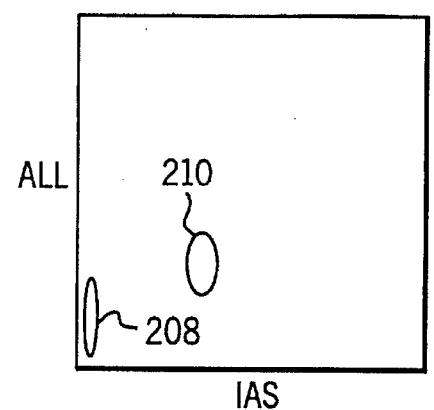
FIGS. 6A, 6B and 6C are drawings of the NRBC, RBC stroma and other background noise distribution of a whole blood sample processed as described in EXAMPLE 1 utilizing only a fluorescence (FL3) trigger.
Figure 5B:
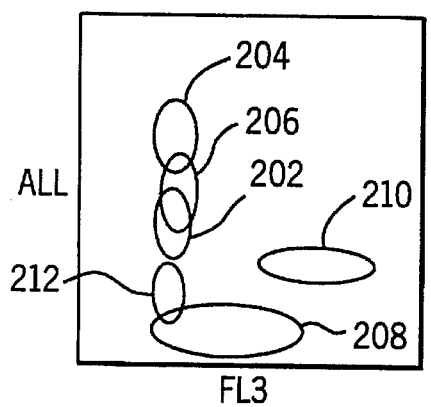
Figure 6B:
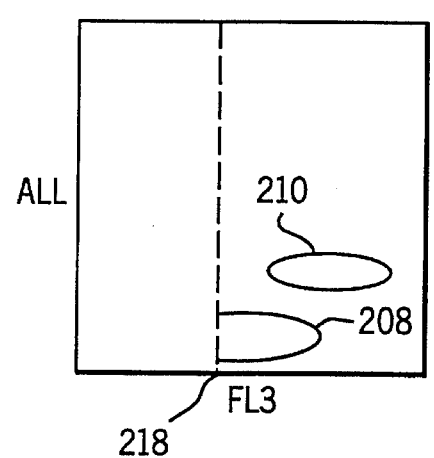
Figure 5C:
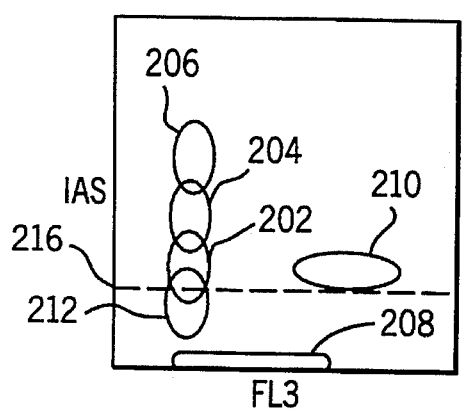
Figure 6C:
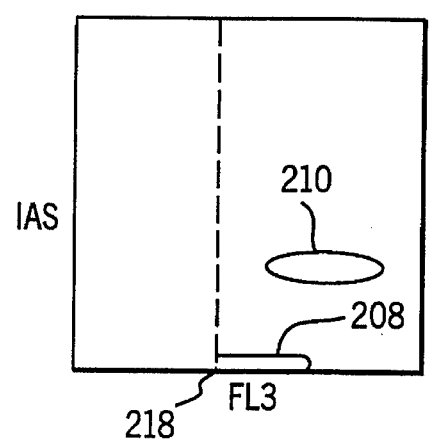
Figure 7A:
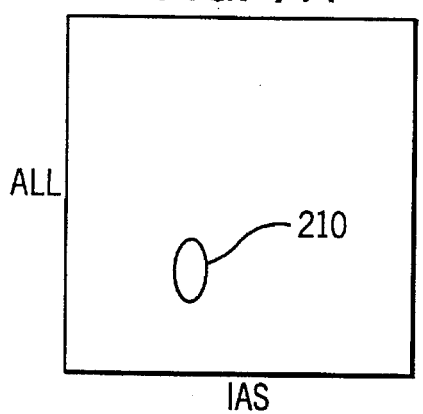
FIGS. 7A, 7B and 7C are drawings of the NRBC distribution of a whole blood sample processed as described in EXAMPLE 1 utilizing a trigger level for FL3 higher than for the trigger utilized in FIG. 6 to eliminate the noise signals.
Figure 8A:
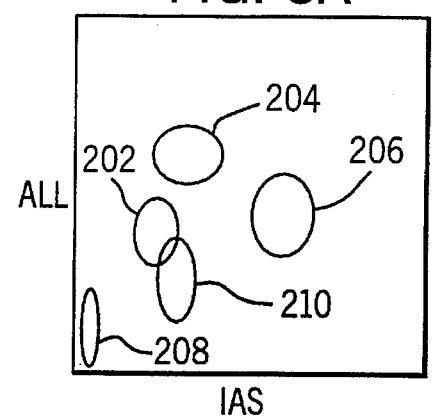
FIGS. 8A, 8B and 8C are drawings of the WBC, NRBC and other background noise distribution of a whole blood sample processed as described in EXAMPLE 1 utilizing two triggers, ALL and FL3, electronically "OR'ed" together.
Figure 7B:
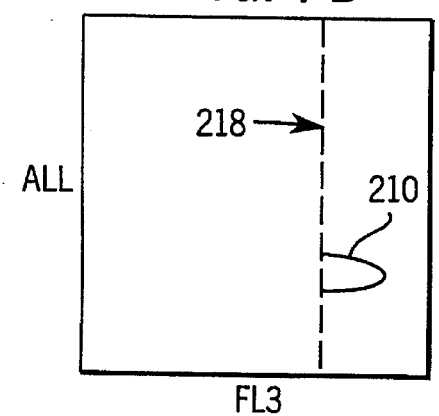
Figure 8B:
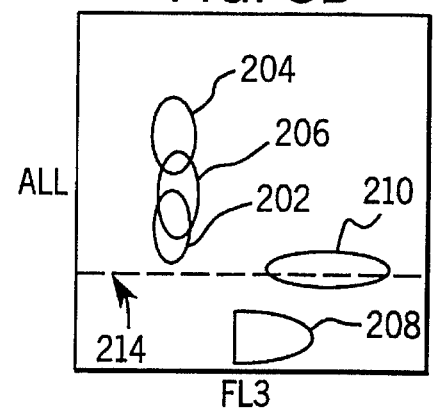
Figure 7C:
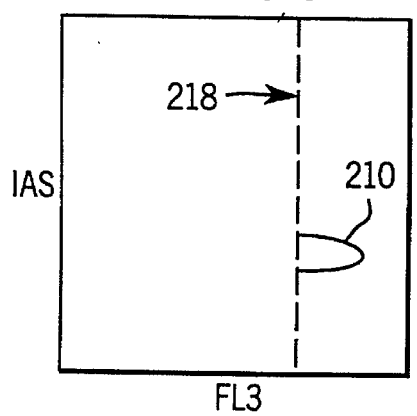
Figure 8C:
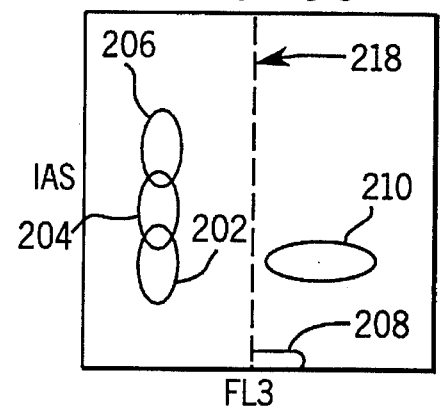
Figure 9A:
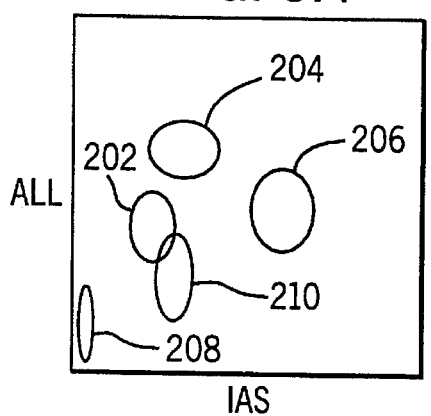
FIGS. 9A, 9B and 9C are drawings of the WBC and NRBC distribution of a whole blood sample processed as described in EXAMPLE 1, utilizing two triggers ALL and FL3 electronically "OR'ed" together with the level of FL3 trigger set at a higher value than in FIG. 8.
Figure 10A:
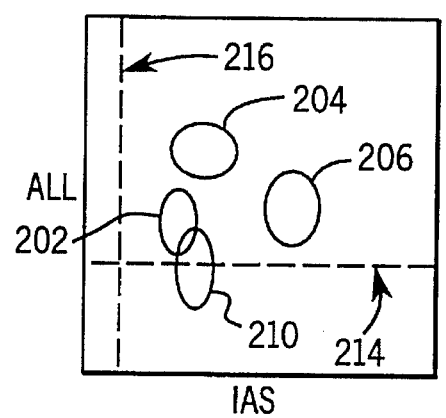
FIGS. 10A, 10B and 10C are drawings of the WBC and NRBC distribution of a whole blood sample processed as described in EXAMPLE 1, with triggers for ALL, IAS and FL3.
Figure 9B:
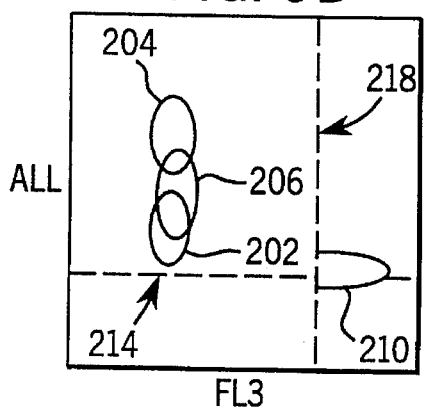
Figure 10B:
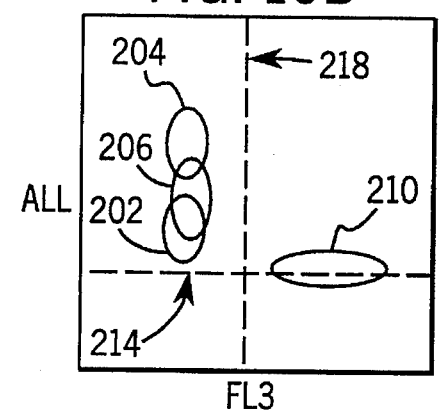
Figure 9C:
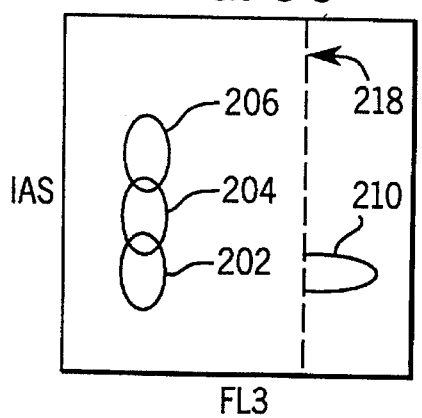
Figure 10C:
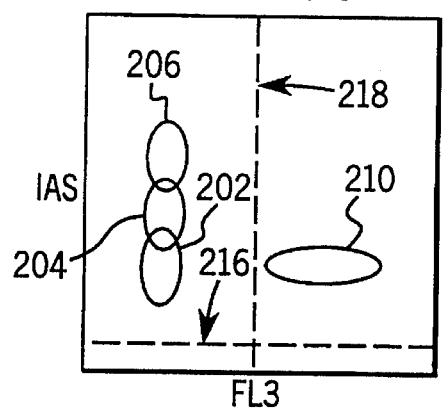

FIG. 17 shows the correlation plot of NRBC counts (ordinate) of 85 clinical samples obtained by the method of the current invention. The results were correlated to that of reference manual microscopic counts (abscissa). For manual NRBC counts, 200 cell WBC differential was performed on each patients' blood smears stained with Wright-Giemsa and NRBC counts present in the same region were divided by 2 to report NRBC/100 WBC. Correlation coefficient (R) is 0.973 ($R2=0.946$), the slope is 0.86 and Y-intercept is 1.32.

What is claimed is:

1. A method of differentiating nucleated red blood cells (NRBC) from other cells by flow cytometry which comprises:

(a) mixing an aliquot of a blood sample with a lysing reagent system and a vital nuclear stain to stain the nuclei of the NRBC wherein the lysing reagent system comprises a red blood cell (RBC) lysing component, and a leukocyte preserving component wherein the leukocyte preserving component preserves leukocyte cellular membranes to prevent leukocyte staining by the vital nuclear stain;

(b) passing the mixed aliquot, substantially a cell at a time, through an area of optical stimulation;

(c) obtaining for each cell at least one signal for the parameters of fluorescence (FL) and scattered light at both a first and second range of scatter angles;

(d) qualifying the signals obtained by subjecting the signals to a logic wherein a signal, to be qualified, must be greater than a second scatter signal threshold, while at the same time the signal must be greater than either a first scatter signal threshold or a FL threshold wherein the thresholds are set to eliminate spurious FL noise signals and include NRBC population signals in the qualified signals obtained;

(e) constructing a three-dimensional plot of intensity signals of FL and scattered light at both the first and second range of scatter angles from the obtained and qualified signals; and (f) differentiating the NRBC and white blood cells (WBC) from the constructed three-dimensional plot and the qualified signals and determining the number of cells of each.

2. The method of claim 1 wherein the first range of scatter angles is from about 0° to about 1°.

3. The method of claim 1 wherein an obtained signal parameter comprises axial light loss (ALL).

4. The method of claim 3 wherein the ALL is obtained at an angle from about 0° to about 1°.

5. The method of claim 1 wherein the second range of scatter angles is from about 3°–10°.

6. The method of claim 1 wherein the nuclear stain is selected from the group of vital stains consisting of propidium iodide (PI), ethidium bromide (EBr), ethidium homodimer-1 (EthD-1), ethidium homodimer-2 (EthD-2) and diethylene triamine (DTA).

7. A method of differentiating nucleated red blood cells (NRBC) from other cells by flow cytometry which comprises:

(a) mixing an aliquot of a blood sample with a lysing reagent system and a vital nuclear stain to stain the nuclei of the NRBC wherein the lysing reagent system comprises a red blood cell (RBC) lysing component, and a leukocyte preserving component wherein the leukocyte preserving component preserves leukocyte cellular membranes to prevent leukocyte staining by the vital nuclear stain;

(b) passing the mixed aliquot, substantially a cell at a time, through an area of optical stimulation;

(c) obtaining for each cell at least one signal for the parameters of fluorescence (FL) and scattered light at both a range of scatter angles comprising from about 0° to about 1° and about 3°–10°;

(d) qualifying the signals obtained by subjecting the signals to a logic wherein a signal, to be qualified, must be greater than a 3°–10° scatter signal threshold, while at the same time it must be greater than either a 0° to about 1° signal threshold or a FL threshold wherein the thresholds are set to eliminate spurious FL noise signals and include NRBC population signals in the qualified signals obtained;

(e) constructing a three-dimensional plot of intensity signals of FL and scattered light at both the range of scatter angles from the obtained and qualified signals; and (f) differentiating the NRBC and white blood cells (WBC) from the constructed three-dimensional plot and the qualified signals and determining the number of cells of each.

8. The method of claim 7 wherein the nuclear stain is selected from the group consisting of propidium iodide (PI), ethidium bromide (EBr), ethidium homodimer-1 (EthD-1), ethidium homodimer-2 (EthD-2) and diethylene triamine (DTA).

* * * * *